United States Patent [19]

Scherer et al.

[11] 4,151,931

[45] May 1, 1979

[54] ARTICLE DISPENSER APPARATUS FOR USE IN AN AUTOMATED CHEMICAL ANALYZER

[75] Inventors: George W. Scherer; Roger G. Covington, both of Rochester, N.Y.

[73] Assignee: Eastman Kodak Company, Rochester, N.Y.

[21] Appl. No.: 912,290

[22] Filed: Jun. 5, 1978

[51] Int. Cl.$^2$ .................. B65H 1/08; G01N 33/16
[52] U.S. Cl. ............................ 221/226; 422/65; 422/57
[58] Field of Search ............ 23/259, 253 R; 221/279, 221/220, 226, 229, 230, 231, 238

[56] References Cited

U.S. PATENT DOCUMENTS

| | | | |
|---|---|---|---|
| 1,801,165 | 4/1931 | Macke | 221/238 |
| 3,533,744 | 10/1970 | Unger | 23/253 R |
| 3,767,083 | 10/1973 | Webb | 221/279 |
| 3,905,772 | 9/1975 | Hartnett et al. | 23/259 |

Primary Examiner—R. E. Serwin
Attorney, Agent, or Firm—M. S. Sales

[57] ABSTRACT

A container is disclosed for receiving a stack of articles to be sequentially removed from a dispensing station of the container. A stack positioning element in the container has an anti-backup member including a pair of pawls resiliently urged into engagement with cooperating ratchet teeth on opposed inner wall surfaces of the container to inhibit movement of received articles away from the container's dispensing station. The container is adapted to receive a plunger which provides the required force to sequentially move the stack positioning element and article stack toward the dispensing station as articles are removed therefrom. The element is configured so that pressure from the plunger causes a reduction in the force of engagement of the pawls with the ratchet teeth in order to minimize the force required of the plunger to move the element and article stack toward the dispensing station.

7 Claims, 6 Drawing Figures

ARTICLE DISPENSER APPARATUS FOR USE IN AN AUTOMATED CHEMICAL ANALYZER

BACKGROUND OF THE INVENTION

1. Cross Reference to Related Applications

Reference is made to commonly assigned, copending U.S. Pat. Applications Ser. No. 751,912 entitled CHEMICAL ANALYZER, filed in the names of Louis C. Nosco, Anthony P. DiFulvio and Henry S. Adamski on Dec. 17, 1976, now abandoned; Ser. No. 912,665 entitled CONTAINER WITH ARTICLE POSITIONING ELEMENT, filed concurrently herewith in the names of R. G. Covington, S. H. Miller and A. J. Tucker; and Ser. No. 912,288 entitled ARTICLE CONTAINER, filed concurrently herewith in the names of R. G. Covington and S. H. Miller.

2. Field of the Invention

The present invention relates to article containers from which individual articles can be sequentially removed from stacks of articles received in the containers.

3. Description of the Prior Art

In recent years, a number of automated systems have been developed for carrying out quantitative chemical analysis of fluid samples. While many of the commercially available systems utilize liquid reagents and require analyzer equipment having intricate solution handling and transport capabilities, one biological fluid analyzing apparatus in which discrete test slides containing individual dry reagents are metered through the apparatus to receive a drop of biological fluid to be tested is described in commonly assigned, co-pending U.S. Pat. Application Ser. No. 751,912, entitled CHEMICAL ANALYZER filed on Dec. 17, 1976.

As described in that application, the test slides are stacked in containers also called cartridges. Each slide in a particular container has the same, appropriate reagent for a particular test, such as for example a reagent for testing glucose in blood serum. Other containers might house slides for other tests. One or more containers may be received in an appropriate nest of the analyzing apparatus with a spring biased plunger arranged to engage the stack of slides through an opening in the container to urge the slides forwardly toward a dispensing station at one end of the container.

A push blade in the analyzing apparatus enters the container at the dispensing station to remove the leading slide from the container by pushing it through a slot in the container wall. The remaining slides are moved forwardly in the container by the plunger as each preceding slide is removed.

It is foreseeable that, during the operation of such analyzing apparatus, situations might occur in which it would be desirable to take a container from the apparatus nest after some, but not all, of the slides have been removed therefrom. Such situations might include instances wherein a different biological test requiring a different reagent is to be conducted or wherein the slides are to be stored in controlled conditions at the end of a work day. Upon such removal of a container from the nest, the apparatus plunger no longer urges the remaining slides toward the container's dispensing station. As such, the slides would be free to move about within the container; possibly becoming disoriented and causing jams when the container is again loaded into the analyzing apparatus nest.

Accordingly, it has been suggested to provide the container with a stack positioning element behind the last slide. The element includes an anti-backup member which cooperates with ratchet teeth on the container walls such as shown in U.S. Pat. Application Ser. No. 912,665 entitled CONTAINER WITH ARTICLE POSITIONING ELEMENT, filed concurrently herewith in the names of R. G. Covington, S. H. Miller and A. J. Tucker. The apparatus plunger pushes against the element, which in turn ratchets forwardly in a direction to push against the slides to sequentially advance the slides to the dispensing station of the container. When a container having such stack positioning element is removed from the nest of the analyzing apparatus, the element prevents the slides from moving away from the container's dispensing station.

While such a stack positioning element would work to prevent disorientation of the slides, it would also increase the resistance to movement of the slides by the apparatus plunger. A major portion of such additional resistance would be caused by the engagement of the anti-backup member with the ratchet teeth. The additional resistance can, of course, be offset by a similar increase in the force applied by the plunger, but that increase would increase the force to be overcome upon loading full containers into the analyzer apparatus. Perhaps the most serious effect of increasing the plunger force would be the increased resistance encountered by the push blade when it is activated to push the foremost slide from the stack.

SUMMARY OF THE INVENTION

In accordance with the present invention, a container is provided for receiving a stack of articles for sequential movement toward, and removal from, a dispensing station of the container. An anti-backup member on a stack positioning element located behind the article stack prevents movement of the articles away from the dispensing station by resiliently engaging wall structure on the container with a predetermined force. That force is decreased when the stack positioning element is moved toward the dispensing station so as to reduce the resistance to movement of the stack positioning element toward the dispensing station.

In a preferred embodiment of the present invention, a spring-biased plunger urges a stack of slides in such a container forwardly toward the dispensing station. The plunger is a part of the analyzer apparatus and enters the container through an opening in a container wall. A stack positioning element is positioned in the container between the slides and a received plunger so that the plunger pushes against the positioning element to move the element toward the dispensing station as the slides are removed from the container. A plurality of ratchet teeth on the container wall structure cooperate with resiliently urged ratchet pawl means on the positioning element to keep the element in position should the plunger be removed from the container, thereby preventing movement of the slides away from the dispensing station. The stack positioning element and ratchet pawl means are so configured that pressure on the positioning element by the plunger relieves the pressure between the ratchet pawl means and the ratchet teeth. Accordingly, the ratchet mechanism presents less resistance to movement of the positioning element toward the dispensing station of the container than would be the situation if the pressure were not relieved. Accordingly, the spring pressure necessarily applied by the plunger to the stack positioning element to move it toward the dispensing station of the container may be minimized.

The invention, and its objects and advantages, will become more apparent in the detailed description of the preferred embodiment presented below.

BRIEF DESCRIPTION OF THE DRAWINGS

In the detailed description of the preferred embodiment of the invention presented below, reference is made to the accompanying drawings in which.

DESCRIPTION OF THE PREFERRED EMBODIMENT

Figure 1:
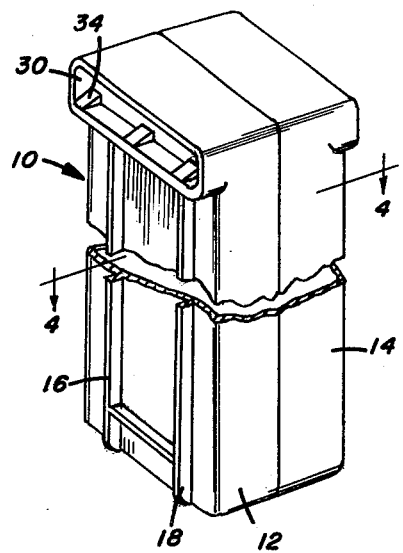
FIG. 1 is a perspective view of a slide container apparatus in accordance with a preferred embodiment of the present invention.
Figure 2:
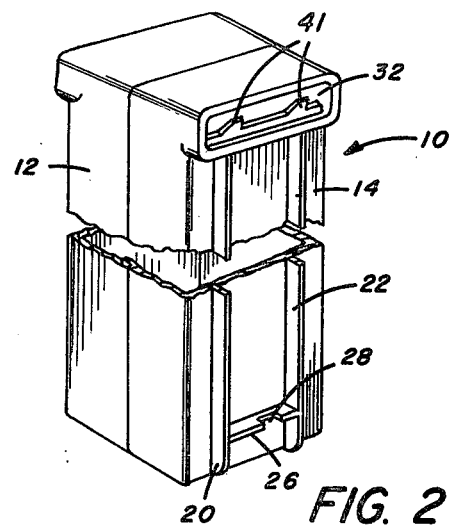
FIG. 2 is a perspective view of the apparatus of FIG. 1 taken from another angle.

In accordance with an illustrative embodiment of the present invention there is shown in FIGS. 1 and 2 a container, designated by the reference numeral 10, adapted to hold a stack of test slides for supply to a chemical analyzer such as the analyzer disclosed in aforementioned U.S. Pat. Application Ser. No. 751,912. Container 10 includes a generally rectangular casing having two parts 12 and 14 shown separated in FIG. 3.

Casing part 12 has a pair of rails 16 and 18, and casing part 14 has a similar, but more closely spaced pair of rails 20 and 22. These rails, and the different spacing thereof insure proper orientation of the container in a nest 24 (FIG. 4) of a chemical analyzer, as described in U.S. Pat. Application Ser. No. 912,288 entitled ARTICLE CONTAINER, filed concurrently herewith in the names of R. G. Covington and S. H. Miller.

Figure 4:
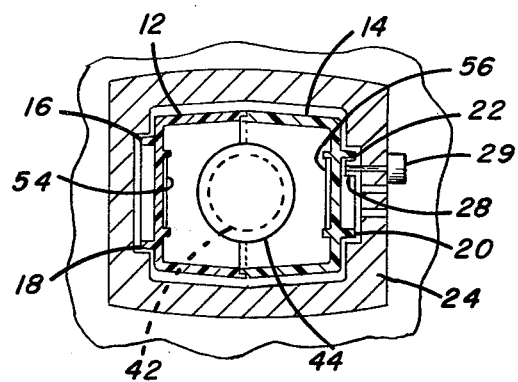
FIG. 4 is a cross-sectional view taken along line 4—4 in FIG. 1 and including a schematic illustration of a nest for the container.

To aid in chemical identification, each container is provided with a notch code system. Referring to FIGS. 2 and 4, a web 26 extends between rails 20 and 22. A portion of web 26 may be removed, such as by punching, to provide a notch 28. The position of the notch along the web is predetermined in accordance with the particular chemical reagent carried by the slides in the container. Mating structure in the analyzer nest is provided to interfere with webs other than those notch coded for the proper reagent for the biological test to be performed. In FIG. 4, such mating structure has been schematically shown as a pin 29 selectively receivable in a plurality of holes. Each hole corresponds to a particular biological test so that insertion of pin 29 into a hole permits reception in the nest of only those containers having notches 28 in web 26 aligned with the hole.

Figure 3:
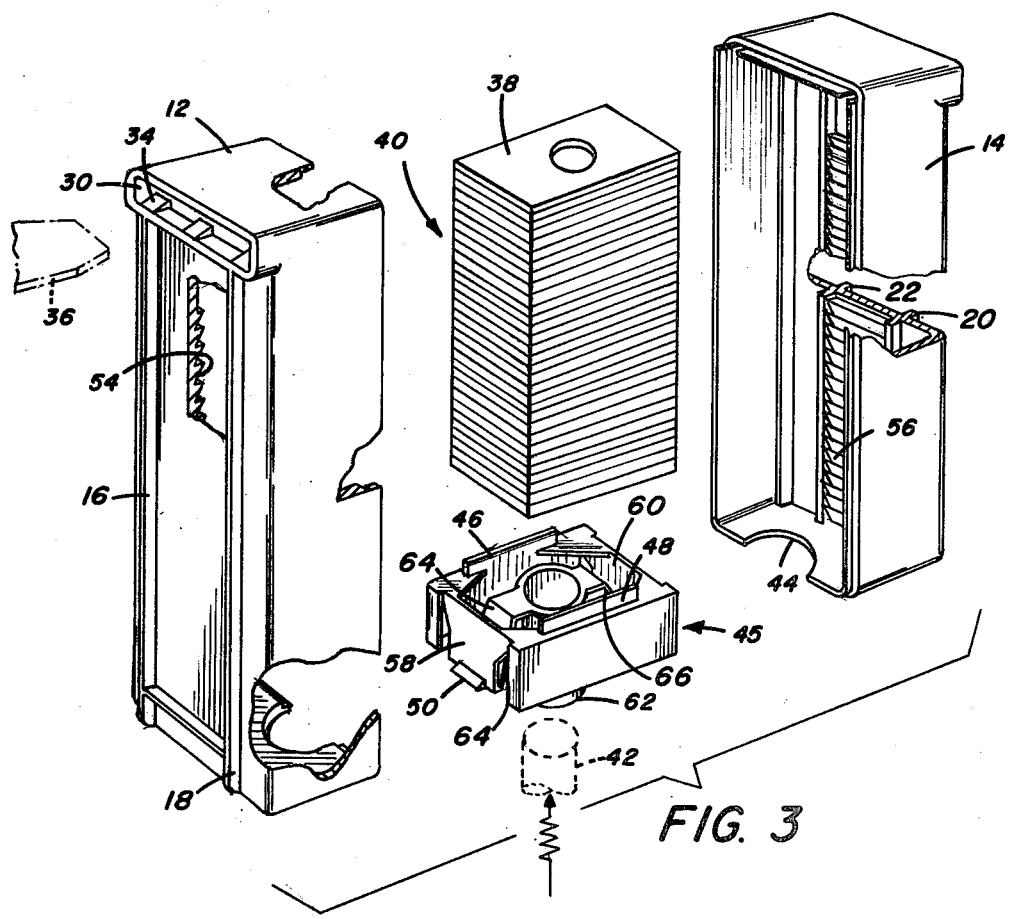
FIG. 3 is an exploded view of the apparatus of FIG. 1 showing a slide stack and a stack positioning element.

A dispensing station at the forward end of container 10 (the top of the container as shown in FIGS. 1–3) includes a pair of slots 30 and 32 for removing slides from the container. Slot 30 is ramped (three ramps 34 shown) to guide a push blade 36 (FIG. 3) of the analyzer into contact with the trailing edge of the foremost slide 38 of a slide stack 40. Slot 32 has a pair of tabs 41 which normally retain the slides in the container until pushed out by push blade 36. The push blade extends through slot 30 to push the foremost slide out of slot 32 and into automatic slide handling means, not shown, of the analyzing apparatus.

When push blade 36 is withdrawn from slot 30, slide stack 40 is indexed forwardly (upwardly in the drawings) by a spring-loaded plunger 42 which extends through an opening 44 in the rear (or bottom) wall of the container to push against a stack positioning element 45. The slide stack rests on a pair of rails 46 and 48 of the stack positioning element. As element 45 moves forwardly toward the dispensing station of container 10, a pair of anti-backup member ratchet pawls 50 and 52 engage successive teeth of ratchet teeth sets 54 and 56 respectively to inhibit movement of the slides away from the dispensing station of container 10 should the container be removed from the analyzer nest after some but not all of the slides have been dispensed therefrom. Upon removal of the container, plunger 42 is withdrawn from opening 44 so that only the ratchet means keeps the slide stack from becoming disoriented.

Accordingly, the ratchet pawls are mounted on flexible, resilient arms 58 and 60 which bias the pawls into engagement with teeth 54 and 56 respectively with sufficient force to maintain such engagement when subjected to a reasonably expected amount of jarring. However, any lateral force applied to the ratchet pawls by arms 58 and 60 must be overcome by push rod 42 to move the slide positioning element forwardly in the container.

As previously mentioned, it is desirable to keep the spring force urging plunger 42 forwardly to a minimum. Accordingly, the present invention provides means for decreasing the lateral force applied to the ratchet pawls when plunger 42 pushes against the stack positioning element, while permitting the maximum lateral force to be applied when the container is not received in the nest of the analyzing apparatus.

Figures 5, 6:
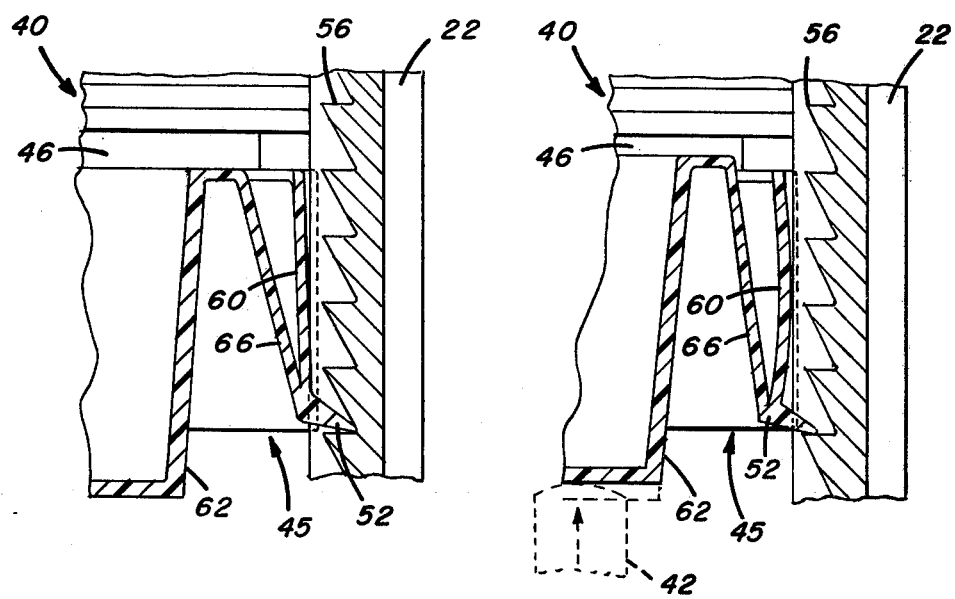
FIG. 5 is a cross sectional view of the stack positioning element of FIG. 3 and a portion of the container.
FIG. 6 is a view similar to FIG. 5 showing the configuration of the stack positioning element when pressure is applied to it by a plunger.

Referring to FIG. 5, a partial cross-sectional view of stack positioning element 45 and one of the container walls shows the cooperation between ratchet pawl 52 and ratchet teeth 56 when the container is removed from the analyzer apparatus. Pawl 52 is urged by flexible arm 60 into the space between the teeth to prevent downward movement of the stack positioning element. The lateral force of arm 60 pushing pawl 52 into engagement with the ratchet teeth is sufficient to prevent the pawls from being jarred from the ratchet teeth during handling.

A hollow cup-shaped member 62 (for storing desiccant) forms a part of stack positioning element 45 and is attached to flexible arms 58 and 60 by a pair of webs 64 and 66 extending from the top of the cup member to the lower ends of arms 58 and 60, respectively. When container 10 is inserted into a nest so that a plunger 42 enters the container through its bottom opening 44, the plunger resiliently pushes against the bottom of cup-shaped member 62. Since rails 46 and 48 rest against the bottom of slide stack 40, the main body of the stack positioning element cannot move upwardly in the container until slides are dispensed. However, cup 62, which is attached to the main body of the positioning element by arms 58 and 60 and webs 64 and 66, is free to move relative to the main body through flexing of arms 58 and 60.

The result of this movement (somewhat exaggerated for clarity) is shown in FIG. 6. Note that plunger 42 has pushed cup 62 upwardly relative to rail 46. Arm 60 has flexed and pawl 52 has moved somewhat out of the space between ratchet teeth 56. Now, as slides are removed from the container, teeth 50 and 52 offer less resistance to upward movement of stack positioning element 45. Therefore, the spring pressure exerted by plunger 42 may be less than would be required if the lateral force on pawls 50 and 52 was not reduced.

When the container is removed from the analyzing apparatus, cup 62 once again returns to its FIG. 5 position relative to rails 46 and 48 so that pawls 50 and 52 are pressed into the recesses between the ratchet teeth and the possibility of the pawls being jarred from the teeth is decreased. It should be noted it is not necessary for pawls 50 and 52 to move entirely out of the spaces between teeth 54 and 56 to reduce the resistance to upward movement of stack positioning element 45 when force is applied to the element to move it toward the dispensing station of container 10.

The invention has been described in detail with particular reference to a preferred embodiment thereof, but it will be understood that variations and modifications can be effected within the spirit and scope of the invention.

What is claimed is:

1. An article container having (1) a dispensing station from which articles are removable; (2) wall structure forming a chamber adapted to receive a stack of articles for sequential movement toward, and removal from, the dispensing station; and (3) a stack positioning element in the chamber movable toward the dispensing station to urge a received article stack toward the dispensing station, whereby the articles are sequentially indexed into the dispensing station as preceding articles in the stack are removed therefrom; said container comprising:
    an anti-backup member on the stack positioning element engageable with the wall structure for inhibiting movement of the stack positioning element away from the dispensing station;
    means for urging said anti-backup member into engagement with the wall structure with a predetermined force; and
    means for decreasing the force between said anti-backup member and the wall structure when the stack positioning element is moved toward the dispensing station to thereby facilitate movement of the stack positioning element toward the dispensing station.

2. The container as set forth in claim 1 wherein said anti-backup member includes:
    an arm flexibly attached at one of its ends to the stack positioning element; and
    a pawl on said arm and spaced from said end for engagement with the wall structure.

3. The container as set forth in claim 2 wherein said force decreasing means includes means for flexing said arm in a direction to move the pawl away from said wall structure.

4. The container as set forth in claim 2 wherein the wall structure comprises a plurality of ratchet teeth engageable by the pawl for inhibiting movement of the stack positioning element away from the dispensing station.

5. For use with apparatus having a plunger, an article container having (1) an article dispensing station (2) a plurality of walls forming a chamber for receiving a stack of articles and (3) means for receiving the plunger to move the articles toward the dispensing station, said container comprising:
    (a) a plurality of ratchet teeth along at least one of the walls; and
    (b) a stack positioning element in the container between a received stack of articles and the plunger receiving means, said stack positioning element including:
        (1) pawl means engageable with said ratchet teeth for inhibiting movement of said stack positioning element away from the dispensing station to prevent movement of the articles away from the dispensing station;
        (2) means for urging said pawl means into engagement with said teeth with a predetermined force; and
        (3) means, engageable by the received plunger, for decreasing the force of engagement of said pawl means and said teeth to facilitate movement of said stack positioning element toward the dispensing station by the plunger.

6. Article dispensing apparatus having a container provided with (1) a dispensing station and (2) a chamber adapted to receive a stack of articles for sequential movement toward the dispensing station; said apparatus comprising:
    a stack positioning element in the container chamber, said element being movable in a direction to urge a received article stack toward the dispensing station of the container, whereby the articles are sequentially indexed into the dispensing station as preceding articles are removed therefrom;
    anti-backup means for inhibiting movement of said stack positioning element away from the dispensing station of the container, said anti-backup means including (1) structure on said container, (2) at least one member on said stack positioning element contactable with said structure for inhibiting movement of said element away from the dispensing station, and (3) means for urging said member into contact with said structure with a predetermined force; and
    means for decreasing the force between said member and said structure when said stack positioning element is moved toward the dispensing station, whereby said force is greater when said element tends to move away from the dispensing station than when said element tends to move toward the dispensing station.

7. An article container for use with apparatus having a plunger, said article container having (1) an article dispensing station (2) a plurality of walls forming a chamber for receiving a stack of articles and (3) means for receiving the plunger to move the articles toward the dispensing station, said container further comprising:
    (a) a plurality of ratchet teeth along at least one of the walls; and
    (b) a stack positioning element in the container between a received stack of articles and the plunger receiving means, said stack positioning element including:
        (1) a first member engageable with the received article stack;
        (2) a second member engageable by the received plunger and movable by the plunger relative to said first member;

(3) pawl means engageable with said ratchet teeth for inhibiting movement of said stack positioning element away from the dispensing station to prevent movement of the articles away from the dispensing station;

(4) resilient means, interconnecting said first member, said second member and said pawl means for urging said first and second members apart and for urging said pawl means into engagement with said teeth with a predetermined force such that the force of engagement of said pawl means and said teeth is decreased by the plunger engaging said second member to facilitate movement of said stack positioning element toward the dispensing station.

* * * * *